United States Patent [19]
Babin et al.

[11] Patent Number: 5,329,017
[45] Date of Patent: Jul. 12, 1994

[54] VINYLSULFONE NOR-PYRETHRIC COMPOUNDS

[75] Inventors: Didier Babin, Montigny; Jean-Pierre Demoute, Neuilly Plaisance; Jean Tessier, Vincennes, all of France

[73] Assignee: Roussel-UCLAF, France

[21] Appl. No.: 51,177

[22] Filed: Apr. 22, 1993

Related U.S. Application Data

[60] Continuation of Ser. No. 499,016, Mar. 26, 1990, abandoned, which is a division of Ser. No. 356,747, May 24, 1989, abandoned.

[30] Foreign Application Priority Data

May 25, 1988 [FR] France ............................ 88 06934

[51] Int. Cl.$^5$ ............................................. C07D 327/04
[52] U.S. Cl. ............................................................ 549/40
[58] Field of Search ............................................ 549/40

[56] References Cited

PUBLICATIONS

Ramos et al, "Chirality and Crop Protection", Angewandte Chemie vol. 30, No. 10, Oct. 1991, pp. 1193 & 1212.

Babin et al, "A New Way . . . ", J. Org. Chem, 1992 vol. 57, 1992 pp. 548–589.

*Primary Examiner*—Johann Richter
*Assistant Examiner*—Catherine S. Kilby Scalzo
*Attorney, Agent, or Firm*—Bierman and Muserlian

[57] ABSTRACT

Novel all possible stereoisomers and mixtures thereof of vinylsulfone nor-pyrethric compounds of the formula

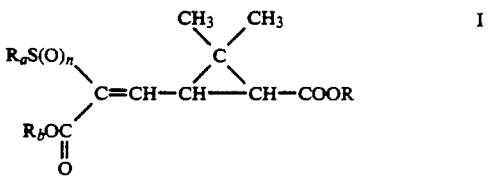

wherein $R_a$ is selected from the group consisting of alkyl of 1 to 18 carbon atoms, alkenyl and alkynyl of 2 to 18 carbon atoms, cycloalkyl of 3 to 18 carbon atoms, cycloalkylalkyl of 4 to 18 carbon atoms and aryl of 6 to 14 carbon atoms unsubstituted or substituted with at least one functional group, n is 0, 1 or 2, $R_b$ is selected from the group consisting of alkyl of 1 to 18 carbon atoms, alkenyl and alkynyl of 2 to 18 carbon atoms, cycloalkyl of 3 to 18 carbon atoms, cycloalkylalkyl of 4 to 18 carbon atoms and aryl of 6 to 14 carbon atoms, all unsubstituted or unsubstituted with at least one functional group or $R_a$ and $R_b$ together with the C-S-C to which they are attached form

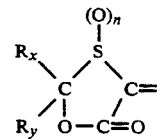

7 Claims, No Drawings

VINYLSULFONE NOR-PYRETHRIC COMPOUNDS

PRIOR APPLICATIONS

This application is a continuation of U.S. patent application Ser. No. 499,016 filed Mar. 26, 1990, now abandoned which is a division of U.S. patent application Ser. No. 356,747 filed May 24, 1989, now abandoned.

STATE OF THE ART

Relevant prior art includes U.S. Pat. No. 4,556,666 and Tetrahedron, Vol. 42 (1986), p. 2475-2484 and Vol. 23 (1982), p. 3265-3266.

OBJECTS OF THE INVENTION

It is an object of the invention to provide the novel compounds of formula I and a process for their preparation.

It is another object of the invention to provide a novel process for the preparation of pesticidally active compounds starting from the compounds of formula I.

These and other objects and advantages of the invention will become obvious from the following detailed description.

THE INVENTION

The novel compounds of the invention are all possible stereoisomers and mixtures thereof of vinylsulfone nor-pyrethric compounds of the formula

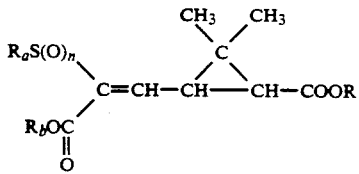

wherein $R_a$ is selected from the group consisting of alkyl of 1 to 18 carbon atoms, alkenyl and alkynyl of 2 to 18 carbon atoms, cycloalkyl of 3 to 18 carbon atoms, cycloalkylalkyl of 4 to 18 carbon atoms and aryl of 6 to 14 carbon atoms unsubstituted or substituted with at least one functional group, n is 0, 1 or 2, $R_b$ is selected from the group consisting of alkyl of 1 to 18 carbon atoms, alkenyl and alkynyl of 2 to 18 carbon atoms, cycloalkyl of 3 to 18 carbon atoms, cycloalkylalkyl of 4 to 18 carbon atoms and aryl of 6 to 14 carbon atoms, all unsubstituted or unsubstituted with at least one functional group or $R_a$ and $R_b$ together with the C—S—C to which they are attached form

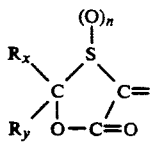

$R_x$ and $R_y$ are individually hydrogen or alkyl of 1 to 4 carbon atoms and R is selected from the group consisting of hydrogen, alkyl of 1 to 8 carbon atoms and the residue of an alcohol used in pyrethrinoid products.

When $R_a$, $R_b$, $R_x$, $R_y$ or R are alkyl, they are preferably methyl, ethyl, n-propyl, isopropyl, n-butyl, sec-butyl, isobutyl, n-pentyl, n-hexyl, tert-butyl, tert pentyl or neo-pentyl.

When $R_a$, $R_b$, $R_x$, $R_y$ or R are cycloalkyl, they are preferably cyclopropyl, cyclobutyl, cyclopentyl or cyclohexyl or a cyclopropyl, cyclobutyl, cyclopentyl or cyclohexyl substituted by at least one alkyl such as 1-methylcyclobutyl, 1-methylcyclopentyl, 1-methylcyclohexyl or 2,2,3,3-tetramethylcyclopropyl or a cycloalkylalkyl such as cyclopropylmethyl.

When $R_a$, $R_b$, $R_x$, $R_y$ or R are alkenyl or alkynyl they may be an ethylene such as vinyl or 1,1-dimethyl alkenyl or alkynyl such as ethynyl or propynyl.

When $R_b$ is alkyl substituted by one or more functional groups, it is preferably alkyl of 1 to 8 carbon atoms such as, methyl, ethyl, propyl, isopropyl, n-butyl, isobutyl or tert-butyl. When $R_b$ is alkyl substituted by at least one functional group, the functional group is preferably halogen, hydroxy or mercapto, alkoxy or alkylthio of 1 to 8 carbon atoms, or nitro or

in which R" and R''' are individually hydrogen or alkyl of 1 to 8 carbon atoms, cyano, —SO$_3$H or —PO$_3$H$_2$ or alk$_1$SO, alk$_2$SO$_2$— or alk$_3$SO$_3$— wherein alk$_1$, alk$_2$ and alk$_3$ are alkyl of 1 to 18 carbon atoms.

$R_b$ can also be alkyl substituted by aryl such as benzyl or phenethyl, itself possibly substituted by at least one hydroxy, alkoxy or alkyl of 1 to 8 carbon atoms, halogen or tri fluoromethyl, trifluoromethoxy, trifluoromethylthio or methylene dioxy. $R_b$ can also be alkyl substituted on two adjacent carbons by a methylenedioxy group or substituted by a 2-tetrahydropyranyloxy group.

When $R_b$ is alkyl substituted by at least one functional group, there can be cited as preferred values for $R_b$: —(CH$_2$)$_n$—C(Hal)$_3$ in which n is an integer from 1 to 8 and Hal is halogen, for example, 2,2,2-trichloroethyl, 2,2,2-trifluoroethyl, 3,3,3-trichloropropyl or 3,3,3-trifluoropropyl; —(CH$_2$)$_{n1}$—CH(Hal)$_2$ in which Hal is defined as above and n$_1$ is an integer from 0 to 8, for example, 2,2-dichloroethyl, 2,2-difluoroethyl or difluoromethyl; —(CH$_2$)$_n$—CH$_2$(Hal) in which n and Hal are defined as above, for example, 2-chloroethyl or 2-fluoroethyl; —C[C(Hal)$_3$]$_3$ in which Hal is defined as above, for example, 2,2,2-trifluoro-1,1-bis(trifluoromethyl) ethyl, or 2,2,2-trichloro-1,1-bis(trifluoromethyl)ethyl; 2,2,2-trifluoro-1-trifluoromethyl-1-methylethyl, 2,2,2-trifluoro-1,1-dimethylethyl or 1-trifluoromethyl-1-methylpropyl; 2,2,2-trifluoro-1-methylethyl or 2,2,2-trifluoro-1-trifluoromethylethyl; 1-cyano-1-methylethyl, 1-cyanoethyl or —(CH$_2$)$_n$—CN in which n is defined as previously; 2,2,2-trihalo-1-cyanoethyl such as for example, 2,2,2-trichloro-1-cyano ethyl; —(CH$_2$)$_n$—OR' in which n is defined as above and R' is hydrogen or alkyl of 1 to 8 carbon atoms, for example, methoxymethyl, 2-methoxyethyl, 2-ethoxyethyl or 2-hydroxyethyl;

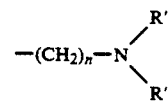

in which n and R' are defined as above and the two R' can be different from each other, for example 2-(methylamino)ethyl, 2-(dimethylamino)ethyl or 2-(ethylmethylamino)ethyl;

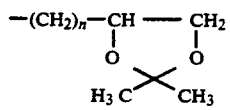

in which n is defined as above, for example

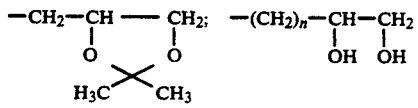

in which n is defined as above, for example 2,3-dihydroxypropyl;

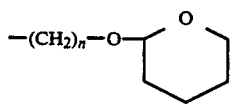

in which n is defined as above, for example (2-tetrahydropyranyloxy)methyl or 2-(2-tetrahydropyranyloxy)ethyl;

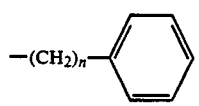

in which n is defined as above, for example benzyl or phenethyl; and

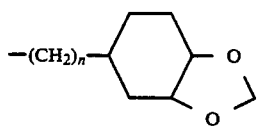

in which n is defined as above, for example, piperonyl.

When $R_b$ is aryl optionally substituted, it is preferred to be phenyl or phenyl substituted by at least one hydroxy or alkoxy of 1 to 8 carbon atoms, or halogen or trifluoromethyl, trifluoromethoxy or trifluoromethylthio.

Among the preferred compounds of the invention, there can be cited the compounds in which n is 2, those in which $R_a$ is tert-butyl, those in which $R_a$ is phenyl or phenyl substituted by $Oalk_1$, $-N(alk_2)_2$, or $alk_3$ and $alk_1$, $alk_2$ and $alk_3$ are alkyl of 1 to 8 carbon atoms.

As preferred values for $R_b$, there can be cited saturated alkyl of 1 to 6 carbon atoms optionally substituted by at least one halogen such as tert-butyl or

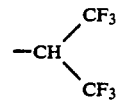

Among the preferred compounds of the invention are those wherein R is saturated alkyl of 1 to 4 carbon atoms such as methyl, ethyl, propyl, isopropyl, n-butyl or tert-butyl.

There can also be cited the compounds in which R is either

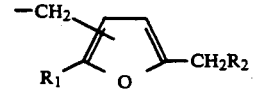

in which $R_1$ is hydrogen or methyl and $R_2$ is monocyclic aryl or 2-propynyl and notably a (5-benzyl-3-furyl)methyl or

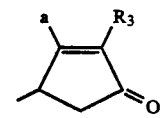

in which a is hydrogen or methyl and $R_3$ is an organic aliphatic of 2 to 6 carbon atoms and one or more carbon-carbon unsaturations and notably $-CH_2-CH=CH_2$, $-CH_2-CH=CH-CH_3$, $-CH_2-CH=CH-CH=CH_2$, $-CH_2-CH=CH-CH_2-CH_3$, or

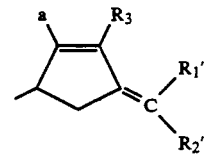

in which a is hydrogen or methyl, $R_3$ has the same significance as above, $R_1'$ and $R_2'$ are individually hydrogen, halogen, alkyl of 1 to 6 carbon atoms, aryl of 6 to 10 carbon atoms, alkyloxycarbonyl of 2 to 5 carbon atoms, or

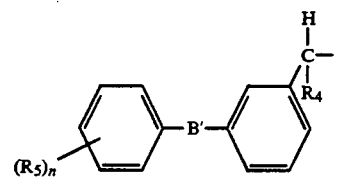

in which B' is oxygen or sulfur, carbonyl, methylene, sulfinyl or sulfonyl, and $R_4$ is hydrogen, cyano, methyl, carbamoyl, thiocarbamoyl or ethynyl, $R_5$ is halogen or methyl and n is 0, 1 or 2, and particularly 3-phenoxybenzyl, α-cyano-3-phenoxybenzyl, α-ethynyl-3-phenoxybenzyl, 3-benzoylbenzyl, 1-(3-phenoxyphenyl) ethyl, or α-thiocarbamoyl-3-phenoxybenzyl, or

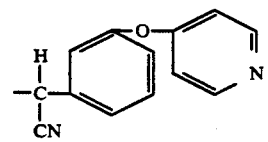

or

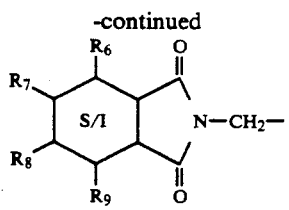

in which the substituents $R_6$, $R_7$, $R_8$, $R_9$ are hydrogen, chlorine, or methyl, and in which S/I symbolizes an aromatic ring or an analogous dihydro or tetrahydro ring, or

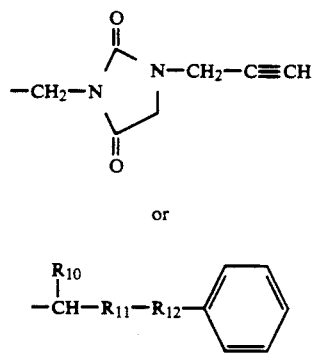

or

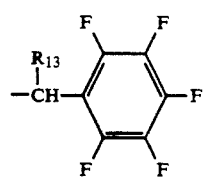

in which $R_{10}$ is hydrogen or cyano, $R_{12}$ is methylene or oxygen, $R_{11}$ is thiazolediyl or thiadiazolediyl bonded to

at any one of the available positions of the ring and to $R_{12}$ by the carbon atom between the sulfur atom and nitrogen atom, or

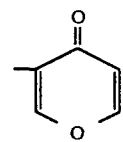

or

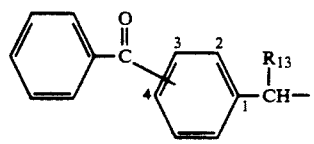

in which $R_{13}$ is hydrogen or cyano, or

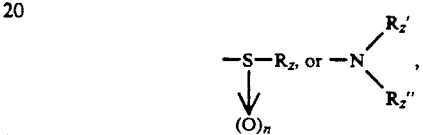

in which $R_{13}$ is defined as above, and the benzoyl is in position 3 or 4, or

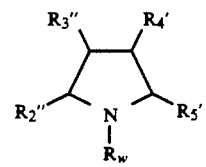

in which one of $R_2''$ or $R_3''$ is —CHZ, Z is hydrogen, cyano, ethynyl, or triflouromethyl or alkyl of 1 to 3 carbon atoms and the other of $R_2''$ or $R_3''$ which is not —CHZ as well as $R_4'$ and $R_5'$ are individually hydrogen, halogen, alkyl of 1 to 18 carbon atoms, aryl of 6 to 14 carbon atoms, aralkyl of 7 to 18 carbon atoms, cyano, trifluoromethyl, alkoxy-carbonyl of 2 to 8 carbon atoms, nitro, alkoxy of 1 to 8 carbon atoms;

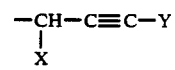

n being equal to 0, 1 or 2 and $R_z$, $R_z'$ and $R_z''$ are alkyl of 1 to 8 carbon atoms, $R_4'$ and $R_5'$ being able also to form a saturated or unsaturated carbonated homocycle of 3 to 8 carbon atoms and $R_w$ is either $$-\underset{X}{CH}-C\equiv C-Y$$

in which X and Y are individually hydrogen, halogen, alkyl of 1 to 8 carbon atoms or aryl of 6 to 14 carbon atoms,

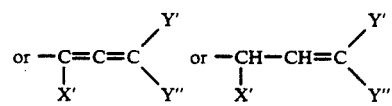

in which X', Y' and Y'' are individually one of the values for X and Y; or

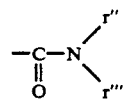

in which r' is hydrogen, alkyl of 1 to 14 carbon atoms, aralkyl of 7 to 18 carbon atoms, trifluoromethyl, alkoxy-carbonyl, alkoxy of 1 to 8 carbon atoms, alkylthio or

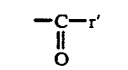

in which r'' and r''' are individually hydrogen, alkyl of 1 to 18 carbon atoms, aryl of 6 to 14 carbon atoms, aralkyl of 7 to 18 carbon atoms, trifluoromethyl, alkoxy-carbonyl of 2 to 8 carbon atoms or alkoxy of 1 to 8 carbon atoms or

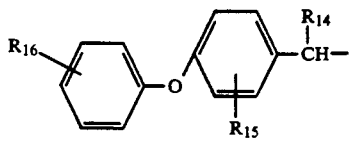

in which $R_{14}$ is hydrogen, methyl, ethynyl or cyano and $R_{15}$ and $R_{16}$ are different and are hydrogen, fluorine or bromine, or

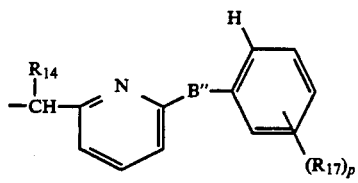

in which $R_{14}$ is defined as previously, B" is oxygen or sulfur, p is 0, 1 or 2, $R_{17}$ is alkyl of 1 to 4 carbon atoms, alkylthio of 1 to 4 carbon atoms, alkylsulfonyl of 1 to 4 carbon atoms, trifluoromethyl, chloro, fluoro or bromo and when p is 2, either $(R_{17})_p$ is methylenedioxy bonded to the phenyl nucleus at positions 3 and 4, or each of the $R_{17}$'s represents independently one of the groups cited above.

Among the preferred compounds are the compounds in which R is

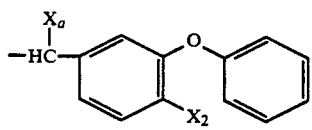

in which $X_a$ is hydrogen, methyl, cyano or ethynyl and $X_2$ is hydrogen or fluorine atom as well as those in which R is

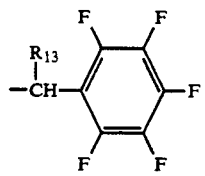

in which $R_{13}$ retains the same significance as above.

The compounds of formula I are those in which the cyclopropane copula is of (1R, cis) or (1R, trans) structure, as well as mixtures of the (1R, cis) and (1R, trans) compounds. The preferred compounds of the invention are those in which the configuration at the cyclopropane is (1R, cis).

The novel process of the invention for the preparation of the compounds of formula I comprises reacting a compound of the formula

in which $R_a$ and $R_b$ have the above definitions and n is 0, 1 or 2 in an alkaline medium with a compound of the formula

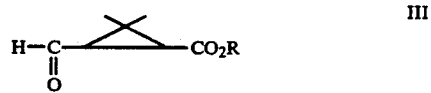

in all its possible stereochemical forms and their mixtures or in the form of a lactone wherein R has the above definition to obtain either the compound of the formula

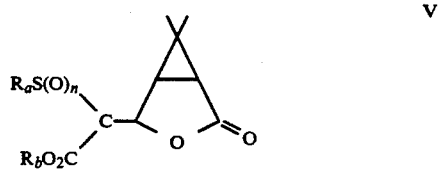

if the compound of formula III is the lactone of (1R, cis)-3-(dihydroxymethyl)-2,2-dimethyl-cyclopropane carboxylic acid, or the compound of formula I if the compound of formula III is not this lactone and the compound of formula V is reacted with an alcohol ROH to obtain the corresponding compound of the formula

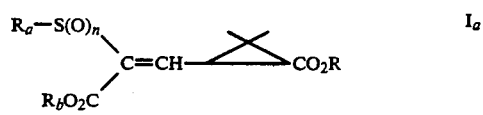

in which R has the above definition with the exception of hydrogen.

The compounds of formula II used as starting products can be prepared by the following reaction scheme:

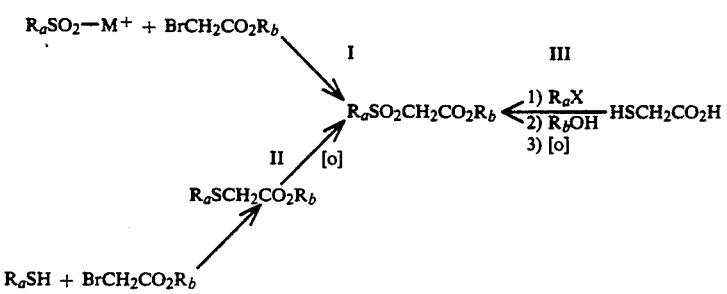

Paths I and II give excellent yields as is shown in the experimental part set out hereafter.

The oxidation of the sulfides is easily done with "oxone" (2KHSO$_5$/KHSO$_4$/K$_2$SO$_4$) or with metachloroperbenzoic acid.

A further object of the invention is the reaction of compounds of formula I

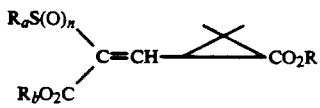

in which R$_a$, R$_b$, R and n have the above definition with a reducing agent to obtain the corresponding compound of the formula

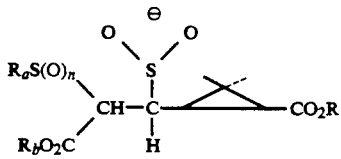

in which R$_a$, R$_b$ and R have the above definitions which is isolated, if desired, or is decomposed spontaneously to give the corresponding compound of the formula

in which R$_b$ and R retain the above definition.

The products of formula V are products known generally and are described, for example, in the European patents No. 0,038,271; No. 0,041,021 and No. 0,048,186. As indicated in these patents, the most interesting products of formula V from a biological view-point are the products in which the geometry of the double bond is Z. The experimental part set out hereafter shows clearly that the products of formula V prepared by the invention are for the most part products with Z geometry.

In a preferred method of application of the invention, the reducing agent is chosen from the following group of anions: S$_2$O$_4^-$, HS$^-$, SO$_3^-$, I$^-$, SCN$^-$, CN$^-$, alk$_4$S$^-$, (alk$_5$)$_3$Si$^-$ or (alk$_6$)$_3$Sn$^-$, alk$_4$, Alk$_5$ and Alk$_6$ are alkyl of 1 to 8 carbon atoms. As preferred reducing agent are those particularly S$_2$O$_4^-$ or any other source of HSO$_2^-$ or SO$_2^-$.

As an example of the invention, the process is characterized in that the reducing agent is sodium dithionite, Na$_2$S$_2$O$_4$, in a mixture of water and an organic solvent, possibly with a phase transfer agent. Phase transfer agents are the salts of tricaprylmethylammonium, of tetrabutylammonium, of triethylbenzylammonium or of any other quaternary ammonium salt as well as phosphonium salts.

When the operation is done in the absence of a phase transfer agent, the reaction is slower and if desired, after acidifying the reaction medium, for example, with a mineral acid such as hydrochloric acid, a methylation agent such as diazomethane can be reacted to isolate the product of formula IV in the form of methyl sulfinate.

The products of formula IV are new products, and the invention also has as object the products of formula IV as new intermediates.

In the following examples there are described several preferred embodiments to illustrate the invention. However, it is to be understood that the invention is not intended to be limited to the specific embodiments.

EXAMPLE 1

(S)-α-cyano-3-phenoxy benzyl (1R,cis) 2,2-dimethyl-3-[(E)-3-tertbutoxy-2-(tert-butyl-sulfonyl)-3-oxo-1-propenyl]-cyclopropanecarboxylate STEP A:
(1R,cis)-4-[2-tert-butoxy-1-(tert-butylsulfonyl)-2-oxoethyl]-6,6-dimethyl-2-oxo-3-oxabicyclo[3.1.0]hexan-2-one At 20° C., 3.5 g of sodium hydride at 50% in oil were added to a solution of 17.25 g of (tert-butylsulfonyl-tert-butyl) acetate and 175 ml of tetrahydrofuran followed by stirring for half-an-hour at 20° C. 10 ml of dimethylformamide were added and stirring was maintained for two hours. Then 10.37 g of the lactone of (1R,cis) dihydroxymethyl-2,2-dimethyl-cyclopropanecarboxylic acid were added and the mixture was stirred for 18 hours at 20° C., then heated for 5 hours at 50° C. The mixture was poured into a saturated solution of sodium acid phosphate. After decanting, the organic phase was concentrated and the product was purified by chromatography on silica. Elution with a hexane-ethyl acetate mixture (1—1) yielded 9.2 g of the expected product.

NMR Spectrum (CDCl$_3$, 60 MHz): 1.22 ppm: twinned methyls of the ring. 1.5 ppm: tert-butyl 1.95–2.05 ppm: 1-hydrogen of the ring. 2.43 ppm: 3-hydrogen of the ring. 4.18 ppm to 4.47 ppm: O—CH—CH—

STEP B: (S)-α-cyano-3-phenoxybenzyl (1R,cis)-3-[(E)-2,2-dimethyl-3-[tert-butoxy-2-(tert-butylsulfonyl)-3-oxo-1-propenyl]-cyclopropane-carboxylate 1.87 g of (S)-α-cyano-3-phenoxybenzyl alcohol were added to a solution of 3 g of the product of Step A in 25 ml of methylene chloride. The mixture was cooled to 10° C. and over 30 minutes, 1.75 g of dicyclohexylcarbodiimide and 50 mg of 4-dimethylamino-pyridine in 50 ml of methylene chloride were added dropwise. The mixture was stirred for 18 hours at 20° C. and was then filtered and concentrated. 5 g of a product were obtained which was chromatographed on silica and eluted with a hexane-isopropyl ether (4–6) mixture to obtain 3.5 g of the expected product melting at 102° C.

EXAMPLE 2

3-phenoxy-benzyl (1R,cis) 2,2-dimethyl-3-[(E)-3-tert-butoxy-2-(tert-butylsulfonyl)-3-oxo-1-propenyl]-cyclopropanecarboxylate 3.5 g of m-phenoxy-benzyl alcohol were added to a solution of 6.3 g of (1R,cis)-4-[2-tert-butoxy-1-(tert-butylsulfonyl)-2-oxo-ethyl]-6,6-dimethyl-2-oxo-3-oxabicyclo[3.1.0]hexan-2-one (cf. Step A of Example 1) and 50 ml of methylene chloride and after the mixture was cooled to +10° C. 3.6 g of dicyclohexylcarbodiimide and 120 mg of 4-dimethylamino-pyridine in solution in 60 ml of methylene chloride were added over half-an-hour. The reaction mixture was stirred for 18 hours at 20° C. and was then filtered and concentrated. 10 g of oil were obtained which, after chromatography and elution with a hexaneisopropyl ether mixture (4–6) yielded 6.35 g of the expected product melting at 72° C.

EXAMPLES 3 to 14

Using the procedure of one of the preceding examples, the following products were prepared:

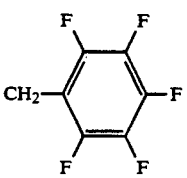

| $R_aS(O)_n$ | $R_b$ | R |
|---|---|---|
| In series 1Rcis | | |
| $C_6H_5SO_2$ | tbu | $CH_3$ |
| 4-MeO $C_6H_4SO_2$ | tbu | $CH_3$ |
| 4-$NH_2$ $C_6H_4SO_2$ | tbu | $CH_3$ |
| 4-$NMe_2C_6H_4SO_2$ | tbu | $CH_3$ |
| 4-MeO $C_6H_4SO_2$ | tbu | 3-phenoxybenzyl |
| 2-MeO $C_6H_4SO_2$ | tbu | 3-phenoxybenzyl |
| 2-Meo $C_6H_4SO_2$ | tbu | 3-phenoxybenzyl |
| $C_6H_5SO$ | tbu | 3-phenoxybenzyl |
| $C_6H_5SO_2$ | Et | $CH_3$ |
| $C_6H_5SO_2$ | Me | (2,3,5,6-tetrafluorobenzyl) |
| $CH_3SO_2$ | tbu | $CH_3$ |
| In series 1R trans | | |
| $C_6H_5SO$ | tbu | 3-phenoxybenzyl |

EXAMPLE 15

(S) α-cyano-3-phenoxy-benzyl
(1R,cis)-2,2-dimethyl-3-[(Z)-3-tert-butoxy-3-oxo-1-propenyl]-cyclopropanecarboxylate 9 ml of pH 8.5 buffer obtained by mixing 8.3 g of potassium acid phosphate, 50 ml of water and 56 ml of a normal sodium hydroxide solution were added to a solution of 900 mg of (S) α-cyano-3-phenoxy-benzyl (1R,cis)-2,2-dimethyl-3[(E)-3-tert-butoxy-2-(tertbutyl-sulfonyl)-3-oxo-1-propenyl]cyclopropanecarboxylate in 9 ml of a cyclohexane solution of 162 g/l of tricaprylmethyl-ammonium or Aliquat ® 336. 560 mg of sodium dithionite were added and the reaction mixture was stirred for 15 minutes at 20° C., then heated to reflux for 90 minutes. After cooling, extraction was done with methylene chloride and the extracts were washed with water, dried, and evaporated under vacuum to obtain 2 g of product which was chromatographed on silica. Elution with an 8-2 mixture of cyclohexane and ethyl acetate yielded 400 mg of isomer Z and 20 mg of isomer E of the expected product. Thus, the Z/E ratio was 95/5.

NMR Spectrum, 60 MHz 1.23–1.25 ppm: twinned methyls of the ring. 1.47 ppm: tert-butyl 1.95–2.09 ppm: 1-hydrogen of the ring 3.1–3.26–3.41 ppm: 3-hydrogen of the ring 5.98 ppm: benzyl hydrogen 5.68–5.87 ppm: 2-hydrogen of the 1-propenyl (Z) 6.2–6.55 ppm: 1-hydrogen of the 1-propenyl. 6.88 to 7.5 ppm: aromatic hydrogens.

EXAMPLE 16

3-phenoxy-benzyl (1R,cis)
3-[(Z)-2,2-dimethyl-3-tert-butoxy-3-oxo-1-propenyl]-cyclopropanecarboxylate 3 ml of distilled water, 210 mg of sodium dithionite and 126 mg of sodium bicarbonate were added to a solution of 320 mg of 3-phenoxy-benzyl (1R,cis) 2,2-dimethyl-3-[(E)-3-tert-butoxy-2-(tertbutylsulfonyl)-3-oxo-1-propenyl-cyclopropanecarboxylate and 3 ml of a cyclohexane solution of 162 g/l of tricaprylmethylammonium or Aliquat ® 336. The mixture was refluxed for 75 minutes, then cooled and the organic phase was extracted with methylene chloride. The organic phase was washed with water, dried and evaporated under reduced pressure to obtain 0.7 g of crude product which was chromatographed on silica. Elution with a 9-1 mixture of hexane and ethyl acetate yielded 157 mg of Z ester and 13 mg of E ester of the expected product. The Z/E ratio of the product was therefore about 92/8.

EXAMPLE 17A 3-phenoxy-benzyl (1R,cis)
2,2-dimethyl-3-[(Z)-3-tert-butoxy-3-oxo-1-propenyl]-cyclopropanecarboxylate Using the procedure of Example 16 but with the reaction medium homogeneous and constituted by a mixture of THF, methanol and water without the transfer agent, the reaction mixture was heated for 3 hours at 60° C. The expected product sought was obtained in a yield of 69%.

Ratio Z/E=95/5.

This example illustrates the application of the invention in the case where the operation is done in homogeneous phase.

EXAMPLE 17B 3-(phenoxy-phenyl)-methyl 1R (1α, 3α)-2-2,dimethyl-3-[1-methoxysulfinyl-2-tert-butylsulfonyl-3-(1,1-dimethylethoxy)-3-oxopropyl]-cyclopropanecarboxylate 27 ml of water and 27 ml of methanol were added to a solution of 3 g of (S) (3-phenoxy-phenyl)-methyl (1R,cis) 2,2-dimethyl-3-[(E)-3-tert-butoxy-2-(tert-butylsulfonyl)-3-oxo-1-propenyl]-cyclopropanecarboxylate in 55 ml of tetrahydrofuran. At 20° C., 1.34 g of sodium dithionite dissolved in 30 ml of water were added dropwise over 30 minutes and the solution including the sulfinate ion was stirred for 1 hour. Then, the methanol and the tetrahydrofuran were eliminated under reduced pressure and the remaining aqueous phase was cooled to +5° C., acidified to pH 1 with 0.8 ml of 11.8 N hydrochloric acid, extracted with ethyl ether, washed with an aqueous solution of sodium chloride, dried and concentrated at 25° C. under reduced pressure. 3.4 g of the residue were dissolved in 40 ml of methylene chloride, cooled to +10° C. and 40 ml of a solution of diazomethane in methylene chloride were added dropwise with stirring for 15 minutes, followed by concentrating to dryness under reduced pressure. The residue was chromatographed on silica, (eluant hexane-ethyl acetate, 7-3) to obtain 2 g of the expected product (mixture of 4 isomers). This example illustrates the isolation of the intermediate of formula IV where the operation is done in homogeneous phase.

EXAMPLES 18 to 29

The products of formula V have been prepared by operating as in Examples 15 and 16 according to the reaction scheme:

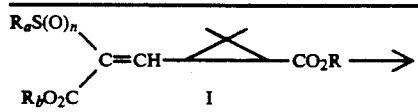

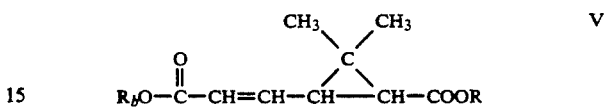

| $R_aS(O)_n$ | $R_b$ | R | Z/E | Yield |
|---|---|---|---|---|
| In series 1R cis | | | | |
| $C_6H_5SO_2$ | tbu | $CH_3$ | 60/40 | 71% |
| 4-MeO $C_6H_4SO_2$ | tbu | $CH_3$ | 74/26 | 70% |
| 4-$NH_2$ $C_6H_4SO_2$ | tbu | $CH_3$ | 71/29 | 66% |
| 4-$NMe_2C_6H_4SO_2$ | tbu | $CH_3$ | 65/35 | |
| 4-MeO $C_6H_4SO_2$ | tbu | 3-phenoxy benzyl | 78/22 | 70% |
| 2-MeO $C_6H_4SO_2$ | tbu | 3-phenoxy benzyl | 85/15 | 60% |
| 2-MeO $C_6H_4SO$ | tbu | 3-phenoxy benzyl | 80/20 | |
| $C_6H_5SO$ | tbu | 3-phenoxy benzyl | 86/14 | 43% |
| $C_6H_5SO_2$ | Et | $CH_3$ | 33/66 | 70% |
| $C_6H_5SO_2$ | Me | 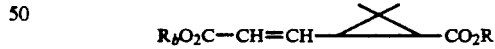 | 34/64 | 73% |
| $CH_3SO_2$ | tbu | $CH_3$ | 14/86 | 45% |
| and in series 1R trans | | | | |
| $C_6H_5SO$ | tbu | 3-phenoxy benzyl | 100/0 | 50% |

The operational conditions were as follows: 1 mmole of product 1, 2 equivalents of $Na_2S_2O_4$ (titer 75–80%), 2 equivalents of $NaHCO_3$, 2 equivalents of tricaprylmethylammonium chloride, 5 ml of water and 5 ml of cyclohexane: refluxing time: 1 hour.

Preparation 1: tert-butyl (tert-butylsulfonyl) acetate

STEP A: Tert-butyl (tert-butylthio) acetate

A solution of 9 g of tert-butylthiol and 100 ml of tetrahydrofuran was cooled to +10° C. and over 15 minutes, 11.2 g of potassium tert-butylate in solution in 150 ml of tetrahydrofuran were added. After stirring for 5 minutes at +10° C., 19.5 g of tert-butyl bromoacetate in solution in 50 ml of tetrahydrofuran were added over 15 minutes at the same temperature. The mixture was stirred for 1 hour at 20° C. and then 75 ml of water were added and the mixture was saturated with sodium chloride. The organic phase was decanted, dried and concentrated under reduced pressure to obtain 20 g of the expected product which was used as is in the following step.

STEP B: Tert-butyl (tert-butylsulfonyl) acetate 92 g of oxone in solution in 400 ml of water were introduced into a solution of 20 g of the product of Step A in 300 ml of methanol, and the mixture was stirred for 18 hours at 20° C. The methanol was then evaporated under reduced pressure, and the aqueous phase was extracted with methylene chloride. After drying and concentrating, 21.5 g of the sulfone melting at 70° C. were obtained.

Various modifications of the compounds and process of the invention may be made without departing from the spirit or scope thereof and it is to be understood that the invention is intended to be limited only as defined in the appended claims.

What we claim is:

1. A process for the preparation of a compound of the formula

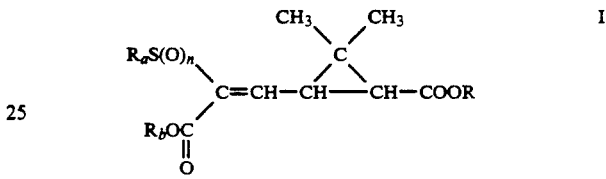

comprising reacting a compound of all possible stereoisomers and mixtures thereof of vinylsulfone norpyrethric compounds of the formula

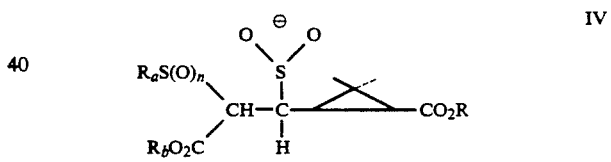

wherein $R_a$ is selected from the group consisting of tert.-butyl and phenyl substituted in position 2 and/or 6 with a functional group, n is 0, 1 or 2, $R_b$ is tert.-butyl and R is selected from the group consisting of hydrogen, alkyl of 1 to 8 carbon atoms and the residue of an alcohol used in pyrethrinoid products with the reducing agent capable of producing $SO_2^-$ to obtain the formula $$R_aS(O)_n\!-\!CH(R_bO_2C)\!-\!C(O^{\ominus})(SO_2)\text{---}CO_2R \quad \text{IV}$$

in which $R_a$, $R_b$ and R have the above definitions which is isolated, if desired, or is decomposed spontaneously to give the corresponding compound of the formula $$R_bO_2C\text{---}CH\!=\!CH\text{---}\triangle\text{---}CO_2R$$

in which $R_b$ and R retain the above definition.

2. The process of claim 1 wherein the reducing agent is an anion selected from the group consisting of $S_2O_4^-$, $HS^-$, $SO_3^-$, $I^-$, $SCN^-$, $CN^-$, $alk_4S^-$, $(alk_5)_3Si^-$ or $(alk_6)_3Sn^-$ and $alk_4$, $alk_5$ and $alk_6$ are alkyl of 1 to 8 carbon atoms.

3. The process of claim 1 wherein the reducing agent is a compound capable of producing $HSO_2^-$ or $SO_2^-$ anions.

4. The process of claim 2 wherein the anion is $S_2O_4^-$.

5. The process of claim 1 wherein the reducing agent is $Na_2S_2O_4$ in a mixture of water and an organic solvent.

6. The process of claim 5 wherein there is present a phase transfer agent.

7. The process of claim 1 wherein $R_a$ is tert.-butyl.

* * * * *